United States Patent [19]

Miller

[11] Patent Number: 4,764,614

[45] Date of Patent: Aug. 16, 1988

[54] PROCESS FOR PREPARING (S)(+)-4,4'(METHYL-1,2-ETHANEDIYL)-BIS(2,6-PIPERAZINEDIONE)

[75] Inventor: William D. Miller, Kettering, Ohio

[73] Assignee: Monsanto Company, St. Louis, Mo.

[21] Appl. No.: 29,038

[22] Filed: Mar. 23, 1987

[51] Int. Cl.$^4$ ..................... A61K 31/50; C07D 403/08
[52] U.S. Cl. ..................................... 544/357; 544/385
[58] Field of Search .................. 544/357, 385; 546/243

[56] References Cited

U.S. PATENT DOCUMENTS 3,941,790  3/1976  Creighton ........................... 544/357
4,275,063  6/1981  Creighton ........................... 514/252

OTHER PUBLICATIONS

Journal of Medicinal Chemistry, vol. 20, No. 5, pp. 630–635, (1977).
Journal of Medicinal Chemistry, vol. 21, No. 12, pp. 1194–1197 (1978).

Primary Examiner—Donald G. Daus
Assistant Examiner—Mark W. Noel
Attorney, Agent, or Firm—Frank D. Shearin

[57] ABSTRACT

The compound (S)(+)-4,4'-(1-methyl-1,2-ethanediyl)-bis(2,6-piperazinedione) is prepared by treating propylenediamine tetraacetic tetraamide in a dipolar aprotic solvent with an alkali metal derivative of dimethyl sulfoxide to form a dialkali metal salt of (S)(+)-4,4'-(1-methyl-1,2-ethanediyl)-bis(2,6-piperazinedione); and neutralizing the dialkali metal salt.

2 Claims, No Drawings

PROCESS FOR PREPARING (S)(+)-4,4'(METHYL-1,2-ETHANEDIYL)-BIS(2,6-PIPERAZINEDIONE)

BACKGROUND OF THE INVENTION

This invention relates to a process for the preparation of (S)(+)-4,4'-(1-methyl-1,2-ethanediyl)bis-(2,6-piperazinedione), which is useful as an active ingredient in a pharmaceutical composition to spare cardiotoxicity of other pharmaceuticals useful for aiding regression and palliation of cancer in mammals.

The usefulness of the above 2,6-piperazinedione is disclosed in U.S. Pat. No. 3,941,790 to Creighton, which also discloses a method in Example 3 of preparing the desired 2,6-piperazinedione by treating d-1,2-diaminopropane tetraacetic acid monohydrate with formamide. The method results in a modest 43% yield before crystallization, and requires vacuum distillation of a high boiling solvent, formamide, to isolate the product. Alternate synthesis methods for other bis-diketopiperazines are described, but when applied to the synthesis of the desired 2,6-piperazinedione of the present invention, yields similar to those of Example 3 were obtained.

In the *Journal of Medicinal Chemistry*, Vol. 20, No. 5, pages 630–635 (1977), and in the *Journal of Medicinal Chemistry*, Vol. 21, No. 12, pages 1194–1197 (1978), Witiak, et. al., describe methods for the preparation of cis- and trans-cyclopropyl-bis-2,6(piperazinediones). The method involves a synthesis of amidoesters of the formula

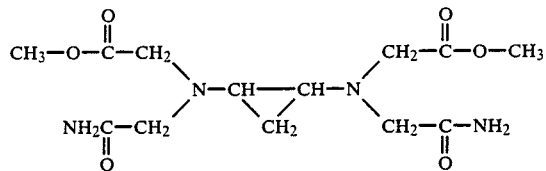

from the corresponding tetramethyl esters of the formula

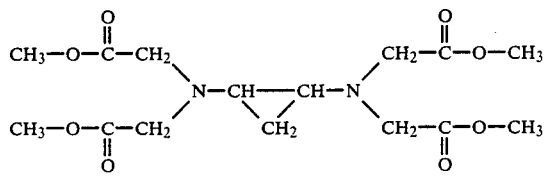

by treating the tetramethyl esters with ammonia or sodium hydride and formamide. The amidoesters were not isolated, but were converted in poor yield into the corresponding 2,6-piperazinediones by treatment with a strong base, such as sodium methoxide or sodium hydride.

Although the prior art processes provide the desired 2,6-piperazinediones, the present invention results in a much higher yield of the desired 2,6-piperazinediones than the previously available methods. In addition, the present invention does not require distillation of a high boiling solvent, such as formamide, which greatly facilitates production of multi-kilogram quantities of the desired product.

SUMMARY OF THE INVENTION

These and other advantages over the prior art are achieved by a process for the preparation of (S)(+)-4,4'-(1-methyl-1,2-ethanediyl)-bis(2,6-piperazinedione) which comprises: treating propylenediamine tetraacetic tetraamide in a dipolar, aprotic solvent with an alkali metal derivative of dimethyl sulfoxide to form a dialkali metal salt of (S)(+)-4,4'-(1,-methyl-1,2-ethanediyl)-bis(2,6-piperazinedione); and neutralizing the alkali metal salt.

The propylenediamine tetraacetic tetraamide can be prepared by methods known to those skilled in the art. Resolution of commercially available propane-1,2-diamine can be achieved by the method of Dwyer, Garvan, and Shulman, *Journal of the American Chemical Society*, 81, pp. 290-294. The resolved S(+)-propane-1,2-diamine can be converted to s(+)-propane-1,2-dinitrilotetraacetic acid in accordance with the teachings of U.S. Pat. No. 2,130,505 to Munz, or U.S. Pat. No. 2,461,519 to Bersworth. The S(+)-propane-1,2-dinitrilotetraacetic acid can be converted to its tetramethyl ester by the procedure of Alner, Claret, and Osborne, *Chemistry and Industry*, November 1968, pp. 1565-1566. The tetramethyl ester may be converted to the desired S(+)-propylene diamine tetraacetic tetraamide by dissolving the ester in methanol, saturating the solution with dry ammonia, and holding the solution at 0°–40° for 24-36 hours.

In the process of the present invention, the desired 2,6-dipiperazinedione is readily synthesized in high yield and without racemization from the propylenediamine tetraacetic tetraamide by treating a solution or suspension of the tetraamide in a dipolar, aprotic solvent, such as dimethyl sulfoxide or dimethyl formamide, with about 2 to about 2.2 molar equivalents of an alkali metal derivative of dimethyl sulfoxide.

Surprisingly, it was found that better yields were obtained when the sodium derivative of dimethyl sulfoxide was used, rather when the potassium or lithium derivative of dimethyl sulfoxide was used, and for the purposes of this disclosure, the sodium derivative will be discussed, but it is understood that the lithium or the potassium derivative is included in such discussions. Hereinafter, the sodium derivative of dimethyl sulfoxide will be referred to as dimsylsodium, which is a common abbreviation for the sodium derivative of dimethylsulfoxide, a reagent commonly used in analytical chemistry for the titration of very weak acids.

The dimsylsodium may be prepared in advance by the reaction of dimethylsulfoxide with an appropriate base, such as sodium amide, sodium hydride, or sodium alkoxide, or generated in situ in a solution or suspension of the propylenediamine tetraacetic tetraamide containing dimethyl sulfoxide, by addition of the base to the solution or suspension. The highest yields of the desired 2,6-piperazinedione is obtained when the dimsylsodium is added to the propylenediamine tetraacetic acid tetraamide solution, or suspension, in several portions over a 2 to 4 hour period. The reaction proceeds at an unacceptably low rate in a dipolar aprotic solvent in the absence of dimethyl sulfoxide. However, the presence of 3%–10% by volume of dimethyl sulfoxide in the suspension or solution results in acceptable reaction rates and reasonably good yields.

As noted above, much better yields are obtained when dimsylsodium is used, rather than when dimsylpotassium or dimsyllithium is employed. These bases resulted in lower yields, the need for longer reaction times, and the reaction mixtures generally contained higher concentrations of undesired reaction by-products.

The reaction temperature can be as low as about 25° C. However, extended reaction times are required at low temperatures. It is preferred to carry out the reaction at a temperature between about 50° C. and about 90° C., more preferably at about 60° C. to about 75° C.

The resulting disodium salt of the desired 2,6-dipiperazinedione has a low solubility in the dipolar aprotic solvent, such as dimethyl sulfoxide and/or dimethyl formamide, and can readily be recovered as a precipitate from the reaction mixture by filtration, centrifugation, or other techniques known to those skilled in the art. A higher yield of the desired disodium-2,6-piperazine dione can be achieved by adding a solvent, such as tetrahydrofuran, to the reaction mixture, and this is what I prefer to do.

The disodium salt of the desired 2,6-piperazinedione can be conveniently neutralized by addition of an acid to the suspension of the disodium salt in tetrahydrofuran, or p-dioxane, or a mixture of tetrahydrofuran and p-dioxane. The neutralized 2,6-dipiperazinedione is soluble in tetrahydrofuran and/or dioxane, and the insoluble salt resulting from the neutralization can be removed by conventional techniques, such as filtration. Most of the reaction by-products are also insoluble in tetrahydrofuran and/or p-dioxane, and can also be removed along with the salt resulting from the neutralization.

The filtrate is then concentrated under reduced pressure, and the concentrate is diluted with methanol or ethanol, or a mixture of the two. The 2,6-dipiperazinedione precipitates, and is recovered by conventional techniques, such as filtration or centrifugation. The resulting 2,6-dipiperazinedione so obtained usually contains from about 2% to about 4% of non-volatile impurities, and can be purified by recrystallization.

The invention is further illustrated, but not limited to the following examples.

EXAMPLE 1

To 30 l of dimethyl sulfoxide was added 2.0 kg of 95% sodium amide (48.6 moles) under a nitrogen atmosphere. The mixture was stirred at 25° C. at atmospheric pressure for 30 minutes, followed by stirring at 25° C. at $6.7 \times 10^3$ Pascals for 15 minutes. The resulting dimsylsodium solution was added in four equal portions over two hours to a stirred solution of 6.85 kg (22.6 moles) of propylenediamine tetraacetic tetraamide in 35 l of dimethyl sulfoxide at 72° C. under a nitrogen atmosphere. The reaction mixture was stirred at 72° C. for an additional 4½ hours. The reaction mixture was cooled to about 23° C., and was diluted with 62 l of tetrahydrofuran. After stirring for two hours, the suspension was filtered to remove the disodium salt of 4,4'-1-(methyl-1,2-ethanediyl-bis(2,6-piperazinedione). The solid was resuspended in 27 l of tetrahydrofuran to remove residual dimethyl sulfoxide. The suspension was filtered to recover the solid. The method was repeated on an additional 6.85 kg quantity of propylene diamine tetraacetic tetraamide and the products of both syntheses were combined for neutralization.

The wet cake of the disodium salt of the 2,6-piperazinedione in tetrahydrofuran was suspended in 114 l of tetrahydrofuran and the suspension was cooled to 18° C. The suspension was stirred under a nitrogen atmosphere, and 9.33 kg (154 moles) of glacial acetic acid were added to the suspension. The suspension was stirred at 25° C. for 2 hours and was diluted with 117 l p-dioxane, followed by heating to 72° C. under a slight nitrogen pressure. The suspension was filtered while still hot in a closed system under nitrogen to remove the sodium acetate formed from the neutralization. The filtrate was concentrated under reduced pressure to a volume of 19 l. The concentrate was cooled to 25° C., and was diluted with 19 l methanol and 3.8 l ethanol. The solution was cooled to 15° C., and was stirred for four hours. The resulting precipitate was removed by filtration and was vacuum dried. The weight of the 2,6-piperazinedione was 8.763 kg and was 92.2% pure and contained the following impurities: Sodium acetate, 2.1%; dimethyl sulfoxide, 3.0%; p-dioxane, 0.7%; and unknown, 2.0%. The yield of the 2,6-piperazinedione from the propylene diamine tetraacetic tetraamide was 66.7%.

Recrystallization of the crude 2,6-piperazinedione from p-dioxane resulted in recovery of 7.520 kg of purified 2,6-piperazinedione in three crops. Yield from propylenediamine tetraacetic tetraamide is 62.1%.

Crop 1, 5.724 kg.
Analysis, calculated for $C_{11}H_{16}N_4O_4$: C, 49.25; H, 6.01; N, 20.89
Found: C, 49.29; H, 6.20; N, 20.81.
Residue on ignition, 0.48%. M.P. 192.5–194° C. $[\alpha]_D^{25} = +39.0°$ (C = 0.5, $H_2O$). $\epsilon_{max} = 34,100$ $\lambda_{max}$ 200 mm.
PMR (DMSO—$d_6$) δ 11.0, doublet (NH); δ 3.35 split peak $$\underset{(C-CH_2N)}{\overset{O}{\parallel}}; \delta\ 3.3-2.9,\ \text{multiplet},\ \underset{(CH-CH_2)}{\overset{O}{|}};\ \delta\ 2.8-2.3,$$

multiplet (N—$CH_3$—$CH_2$—CH); δ 0.89, doublet ($CH_3$—CH).
HPLC, 98.8% by external standard method.
Crop 2, 1.546 kg. Analysis: C, 49.31%; H, 6.06; N, 20.61; R.O.I., 0.074
M.P. 191.5–192.5° C.
$[\alpha]_D^{25} = +39.0°$ (C = .5, $H_2O$. $\epsilon_{max}$ 33,500, $\lambda_{max}$ 200 nm ($H_2O$ HPLC 98.6%.
Crop 3, 0.250 kg, 98% by HPLC.

EXAMPLE 2

Propylenediamine tetraacetic tetraamide (30.0 g, 89% pure, 0.0884 moles) is converted to the desired 2,6-piperazinedione by the procedure of Example 1, except that dimsylsodium is added in 11 portions over 4½ hours and the reaction mixture is heated for an addition 1½ hours. The yield of the desired 2,6-piperazinedione from the propylenediamine tetraacetic tetraamide was 72% before re-crystallization.

Although the invention has been described in terms of specified embodiments which are set forth in considerable detail, it should be understood that this by way of illustration only, and that alternative embodiments and operating techniques will become apparent to those skilled in the art in view of the disclosure. For example, various homologues and sterioisomers can be prepared by adjustments to the starting materials and with modifications to the operating procedure. Accordingly, modifications can be made without departing from the spirit of the described invention.

I claim:
1. A process for the preparation of (S)(+)-4,4'-(1-methyl-1,2-ethanediyl)-bis(2,6-piperazinedione) which comprises:

treating propylenediamine tetraacetic tetraamide in a dipolar aprotic solvent with an alkali metal derivative of dimethyl sulfoxide to form a dialkali metal salt of (S)(+)-4,4'-(1-methyl-1,2-ethanediyl)bis(2,6-piperazinedione); and neutralizing the dialkali metal salt.

2. A process of claim 1 wherein the alkali metal is sodium.

* * * * *